US010448848B2

(12) United States Patent
Park et al.

(10) Patent No.: US 10,448,848 B2
(45) Date of Patent: Oct. 22, 2019

(54) APPARATUS AND METHOD FOR MEASURING BIOINFORMATION

(71) Applicant: Samsung Electronics Co., Ltd., Suwon-si (KR)

(72) Inventors: Sangyun Park, Hwaseong-si (KR); Younho Kim, Hwaseong-si (KR); Yongjoo Kwon, Yongin-si (KR); Seungwoo Noh, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 172 days.

(21) Appl. No.: 15/284,907

(22) Filed: Oct. 4, 2016

(65) Prior Publication Data

US 2017/0095171 A1    Apr. 6, 2017

(30) Foreign Application Priority Data

Oct. 6, 2015   (KR) .................. 10-2015-0140481
Apr. 26, 2016  (KR) .................. 10-2016-0050771

(51) Int. Cl.
*A61B 5/02*  (2006.01)
*A61B 5/024* (2006.01)
(Continued)

(52) U.S. Cl.
CPC ........ *A61B 5/02438* (2013.01); *A61B 5/0022* (2013.01); *A61B 5/0205* (2013.01); *A61B 5/02007* (2013.01); *A61B 5/02125* (2013.01); *A61B 5/02427* (2013.01); *A61B 5/0452* (2013.01); *A61B 5/0535* (2013.01);
(Continued)

(58) Field of Classification Search
CPC .. A61B 5/024; A61B 5/00; A61B 5/02; A61B 5/021; A61B 5/145; A61B 5/0022; A61B 5/7475; A61B 5/742; A61B 5/7271; A61B 5/7225; A61B 5/14542; A61B 5/02438; A61B 5/02427; A61B 5/02125; A61B 5/02007; A61B 5/681; A61B 5/7203; A61B 5/0205; A61B 5/0452;
(Continued)

(56) References Cited

U.S. PATENT DOCUMENTS 6,413,223 B1    7/2002  Yang et al.
7,674,231 B2    3/2010  McCombie et al.
(Continued)

FOREIGN PATENT DOCUMENTS

JP    2005-102959 A    4/2005
JP    2009-72242 A     4/2009

OTHER PUBLICATIONS

European search report issued by the European Patent Office dated Mar. 9, 2017 for the corresponding EP Patent Application No. 16192401.4 (6 pages in English).

*Primary Examiner* — Eric J Messersmith
(74) *Attorney, Agent, or Firm* — NSIP Law

(57) ABSTRACT

An apparatus and a method of measuring bioinformation are provided. The apparatus for measuring bioinformation includes a first sensor configured to measure a first biosignal including arterial pulse wave information, a second sensor configured to measure a second biosignal including venous or capillary pulse wave information, and a bioinformation estimator configured to estimate bioinformation of a user based on a time delay between the first biosignal and the second biosignal.

28 Claims, 11 Drawing Sheets

(51) Int. Cl.

| | | |
|---|---|---|
| *A61B 5/00* | (2006.01) | |
| *A61B 5/021* | (2006.01) | |
| *A61B 5/145* | (2006.01) | |
| *A61B 5/0205* | (2006.01) | |
| *A61B 5/0452* | (2006.01) | |
| *A61B 5/053* | (2006.01) | |
| *A61B 5/1455* | (2006.01) | |
| *G06F 19/00* | (2018.01) | |
| *G16H 40/67* | (2018.01) | |

(52) U.S. Cl.
CPC ...... *A61B 5/14542* (2013.01); *A61B 5/14551* (2013.01); *A61B 5/681* (2013.01); *A61B 5/6823* (2013.01); *A61B 5/6826* (2013.01); *A61B 5/7203* (2013.01); *A61B 5/7225* (2013.01); *A61B 5/7271* (2013.01); *A61B 5/742* (2013.01); *A61B 5/7475* (2013.01); *G06F 19/00* (2013.01); *G16H 40/67* (2018.01); *A61B 2562/0247* (2013.01)

(58) Field of Classification Search
CPC . A61B 5/0535; A61B 5/14551; A61B 5/6823; A61B 5/6826; A61B 2562/0247
See application file for complete search history.

(56) References Cited

U.S. PATENT DOCUMENTS

| | | |
|---|---|---|
| 8,086,301 B2 | 12/2011 | Cho et al. |
| 8,795,185 B2 | 8/2014 | Cho |
| 2006/0161063 A1* | 7/2006 | Shau .................. A61B 5/0261 600/504 |
| 2006/0616063 | 7/2006 | Shau |
| 2007/0270699 A1* | 11/2007 | Crabtree .............. A61B 5/0261 600/500 |
| 2007/0287923 A1 | 12/2007 | Adkins et al. |
| 2008/0039731 A1* | 2/2008 | McCombie ........ A61B 5/02125 600/485 |
| 2008/0202246 A1 | 8/2008 | Suzuki |
| 2009/0093729 A1 | 4/2009 | Zhang et al. |
| 2010/0185068 A1* | 7/2010 | Park ...................... A61B 5/021 600/324 |
| 2010/0210956 A1 | 8/2010 | Im |
| 2012/0059237 A1 | 3/2012 | Amir et al. |
| 2012/0150047 A1 | 6/2012 | Terumoto et al. |
| 2012/0215117 A1* | 8/2012 | Karst ................. A61B 5/02125 600/486 |
| 2013/0289394 A1* | 10/2013 | Hielscher ............. A61B 5/0053 600/425 |
| 2013/0296723 A1 | 11/2013 | Cho et al. |
| 2014/0323895 A1 | 10/2014 | Vitushinsky et al. |
| 2017/0340219 A1* | 11/2017 | Sullivan ............... A61B 5/6824 |

* cited by examiner

… (1)

APPARATUS AND METHOD FOR MEASURING BIOINFORMATION

CROSS-REFERENCE TO RELATED APPLICATIONS

This application claims the benefit under 35 USC 119(a) of Korean Patent Application No. 10-2015-0140481 filed on Oct. 6, 2015, and Korean Patent Application No. 10-2016-0050771 filed on Apr. 26, 2016, in the Korean Intellectual Property Office, the entire disclosure of both of which are incorporated herein by reference for all purposes.

BACKGROUND

1. Field

The following description relates to an apparatus and a method of measuring bioinformation and to a technology for extracting cardiovascular features of a user by analyzing pulse wave signals.

2. Description of Related Art

Representative examples of noninvasive techniques for extracting cardiovascular features of a user without using a blood pressure cuff include a pulse wave analysis (PWA) method and a pulse wave velocity (PWV) method. A PWA method refers to a method in which cardiovascular features of a user is obtained by analyzing a shape of a pulse wave signal measured from a distal end of a body, such as a fingertip. The blood ejected from a left ventricle during a cardiac contraction is partially reflected at locations where large branches such as a renal artery or an infrarenal aorta branch off, and the reflection affects a shape of a pulse wave signal measured at a distal end of the body. Thus, the cardiovascular features of a user may be derived by analyzing the shape of the pulse waveform measured at the distal end. A PWV method, on the other hand, refers to a method in which cardiovascular features of a user is obtained by measuring a pulse wave velocity. A PWV method may include measuring an electrocardiogram (ECG) at a location close to a heart and a pulse wave at a distal end of a body, such as a fingertip, and estimating a user's cardiovascular features based on a delay time between the ECG signal and the pulse wave signal.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for measuring bioinformation includes a first sensor configured to measure a first biosignal including arterial pulse wave information; a second sensor configured to measure a second biosignal including venous or capillary pulse wave information; and a bioinformation estimator configured to estimate bioinformation of a user based on a time delay between the first biosignal and the second biosignal.

The first sensor may be configured to measure the first biosignal from a ventral side of a wrist, and the arterial pulse wave information may include pulse wave information from a radial artery or an ulnar artery.

The second sensor may be configured to measure the second biosignal from a dorsal side of a wrist, and the venous or capillary pulse wave information may include pulse wave information from a vein or a capillary.

The first sensor may be disposed in a strap of a wrist-type wearable device, and the second sensor may be disposed on a back side of a body of the wrist-type wearable device.

The first sensor may include a first light source configured to emit first light to measure a photoplethysmogram, and a first light detector configured to detect first reflected light corresponding to the first light reflected by a body part of the user.

The second sensor may include a second light source configured to emit second light to measure a photoplethysmogram, and a second light detector configured to detect second reflected light corresponding to the second light reflected by a body part of the user. The second light may have a shorter wavelength than the first light.

The first sensor may be configured to measure the first biosignal using at least one selected from a group consisting of a pressure sensor, an impedance sensor, and a piezoelectric element.

The second sensor may be configured to measure the second biosignal using at least one of selected from a group consisting of a pressure sensor, an impedance sensor, and a piezoelectric element.

The bioinformation estimator may be configured to estimate a trend in a change of pulse wave velocity over time based on the time delay between the first biosignal and the second biosignal, and to estimate a change in the bioinformation of the user based on the estimated trend.

The bioinformation estimator may be configured to determine the time delay based on a feature point extracted from a waveform of the first biosignal and a feature point extracted from a waveform of the second biosignal.

The bioinformation estimator may be configured to estimate the bioinformation based on a time delay between a maximum slope point of the waveform of the first biosignal and a minimum slope point of the waveform of the second biosignal.

The bioinformation estimator may be configured to move at least one of a waveform of the first biosignal and a waveform of the second biosignal along a time axis, and determine the time delay based on a similarity between the at least one moved waveform of the first biosignal and the waveform of the second biosignal.

The bioinformation estimator may be configured to estimate at least one of an arterial stiffness, a vascular age, a blood oxygen saturation level ($SpO_2$), a heart rate, and a blood pressure of the user based on the time delay.

In another general aspect, an apparatus for measuring bioinformation includes a first sensor configured to measure a first biosignal including arterial pulse wave information, a second sensor configured to measure a second biosignal including venous or capillary pulse wave information, and a signal processor configured to convert the first biosignal and the second biosignal into respective digital signals.

The signal processor may be configured to amplify the first biosignal and the second biosignal before converting the first biosignal and the second biosignal into the respective digital signals.

The first sensor may be disposed inside a strap of a wrist-type wearable device, and the second sensor may be disposed on a back side of a body of the wrist-type wearable device.

In another example, a method of measuring bioinformation involves measuring a first biosignal including arterial pulse wave information, measuring a second biosignal including venous or capillary pulse wave information, and estimating bioinformation of a user based on a time delay between the first biosignal and the second biosignal.

The measuring of the first biosignal may involve measuring the first biosignal from a ventral side of a wrist of the user, and the arterial pulse wave may include pulse wave information from a radial artery or an ulnar artery.

The measuring of the second biosignal may involve measuring the second biosignal from a dorsal side of a wrist of the user, and the venous or capillary pulse wave information may include pulse wave information from a vein or a capillary.

In another general aspect, a non-transitory computer-readable medium may store instructions that, when executed by a processor, causes a processor to perform the general aspect of method described above.

In yet another general aspect, a wearable device includes one or more sensors configured to detect first pulse wave information from an artery and second pulse wave information from a vein or capillary, and a processor configured to estimate a pulse transit time for a pulse detected in the first pulse wave information to propagate and be reflected in the second pulse wave information.

The processor may be configured to estimate cardiovascular information based on an inverse value of the pulse transit time.

The wearable device may be configured to position each of the one or more sensors on one body location of a user, the one body location corresponding to one selected from a group consisting of an upper arm, a lower arm, a wrist, an upper leg, a lower leg, an ankle and a neck of the user.

In yet another general aspect, a method of measuring bioinformation involves obtaining first pulse wave information from an artery and second pulse wave information from a vein or a capillary, using a processor to estimate a pulse transit time based on the first pulse wave information and the second pulse wave information, and estimating bioinformation based on the estimated pulse transit time.

The obtaining of the first and second pulse wave information may involve using sensors of a wearable device to measure a biosignal.

Both the first pulse wave information and the second pulse information may be obtained from one body location of the user, the one body location corresponding to one selected from a group consisting of an upper arm, a lower arm, a wrist, an upper leg, a lower leg, an ankle and a neck.

The first pulse wave information and the second pulse wave information may be respectively obtained either from a dorsal side and a ventral side or from a ventral side and a dorsal side of a body of a user.

The obtaining of the first pulse wave information and the second pulse wave information may be performed by a wearable device, and the estimating of the bioinformation may be performed by a terminal that wirelessly receives data from the wearable device.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
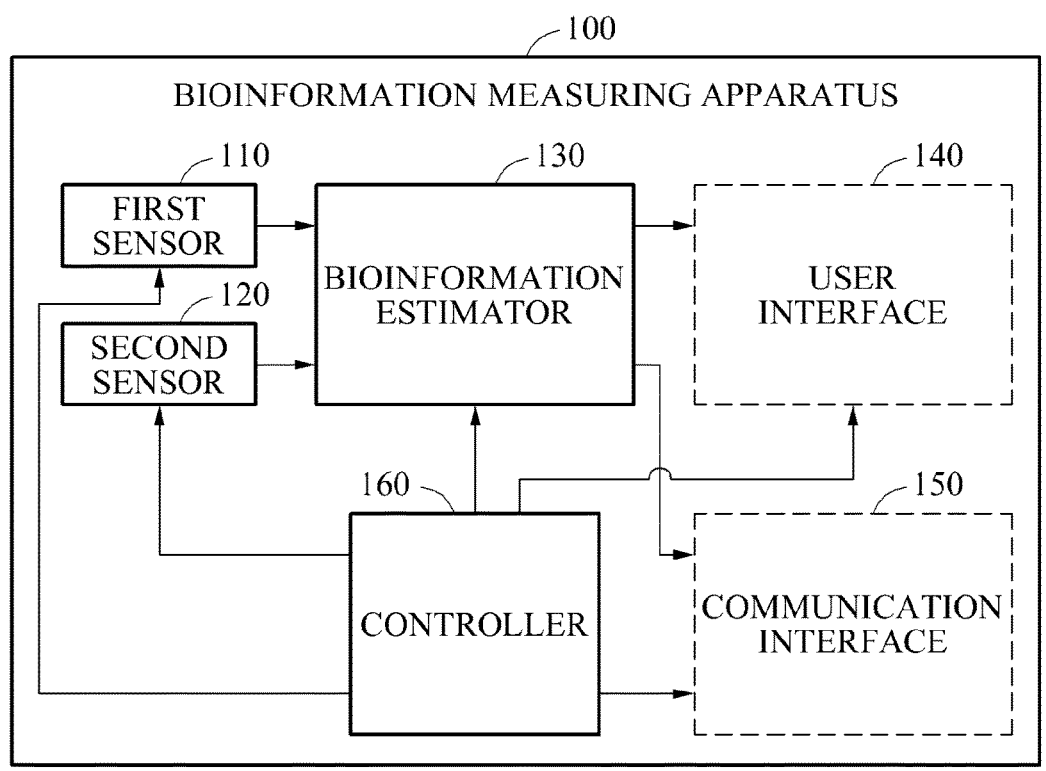
FIG. 1 is a diagram illustrating an example of an apparatus for measuring bioinformation.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing a number of examples only and is not to limit the scope of the disclosure. The articles "a," "an," and "the" are intended to include the plural forms as well, unless the context clearly indicates otherwise. The terms "comprises," "comprising," "includes," "including," "has," and "having" specify the presence of stated features, numbers, operations, elements, components, and combinations thereof, but do not preclude the presence or addition of one or more other features, numbers, operations, elements, components, and combinations thereof.

In addition, terms such as "first," "second," A, B, (a), (b), and the like may be used herein to describe components. These terms are not intended to define an essence, order or sequence of a corresponding component but merely to distinguish the corresponding component from other component(s).

Examples to be described hereinafter provide an apparatus and a method for estimating bioinformation of a user based on biosignals that include pulse wave information. A pulse wave refers to a wave that is generated as a pulse propagates through blood vessels from a heart towards distal parts of the body, and a pulse refers to the repetitive expansion and relaxation of an artery due to the blood being pushed along the artery each time the heart beats. Each time the heart contracts, oxygenated blood is supplied from the heart to the rest of body by first being pumped into the aorta and then to arteries that branches off the aorta. The pumping of the blood causes a change in pressure in the aorta. Such a change in pressure is propagated down the arterial tree to peripheral arterioles found in hands and feet. The change in pressure may be measured and shown as a waveform, which may be referred to as a pulse wave.

Bioinformation includes, for example, cardiovascular information such as a vascular or arterial stiffness, a blood pressure, a vascular age, a heart rate, and a blood oxygen saturation level ($SpO_2$). Arterial stiffness indicates a degree of a stiffness of a blood vessel, and is affected by an elasticity of the blood vessel and a degree of deposits in intimae of the blood vessel. Blood pressure refers to a pressure exerted by circulating blood upon the walls of blood vessels as blood flows from the heart to the rest of the body. Vascular age refers to a physiological age indicating a degree of aging of a blood vessel, and relates to arterial stiffness. Heart rate indicates the number of heart beats per hour. $SpO_2$ indicates a ratio of an amount of hemoglobin bound to oxygen in blood to a total amount of hemoglobin.

Hereinafter, examples will be described in detail with reference to the accompanying drawings. Like reference numerals in the drawings denote like elements, and a known function or configuration will be omitted herein.

FIG. 1 is a diagram illustrating an example of an apparatus for measuring bioinformation. Hereinafter, the apparatus for measuring bioinformation will be referred to as a bioinformation measuring apparatus 100. The bioinformation measuring apparatus 100 measures biosignals from a body of a user, and estimates bioinformation of the user based on the measured biosignals. For example, the bioinformation measuring apparatus 100 may measure biosignals from a body part, such as a wrist of the user, and estimate cardiovascular information of the user based on the measured biosignals. According to one example, the bioinformation measuring apparatus 100 is included in a wearable device that a user may wear throughout day and night. Thus, the bioinformation measuring apparatus 100 may continuously monitor the health condition of the user by estimating the cardiovascular information of the user while the user is wearing the wearable device.

Hereinafter, an example of a method of estimating bioinformation of a user performed by a bioinformation measuring apparatus 100 based on biosignals measured from a wrist of the user will be described. However, the scope of the disclosure is not limited to the examples; the bioinformation measuring apparatus 100 may, for example, measure biosignals from various other body locations such as a forearm, a leg, an ankle, and a neck, and estimate bioinformation based on the measured biosignals. In addition, the bioinformation measuring apparatus may be implemented in a wearable device having a different shape, such as a band that encircles a section of a leg or an arm.

Referring to FIG. 1, the bioinformation measuring apparatus 100 includes a first sensor 110, a second sensor 120, a bioinformation estimator 130, and a controller 160. Operations of the bioinformation estimator 130 and the controller 160 may be performed by at least one processor.

The first sensor 110 measures a first biosignal including arterial pulse wave information. For example, the first sensor 110 may measure the first biosignal including the arterial pulse wave information from at least one of a radial artery and an ulnar artery. In the wrist area, the radial artery and ulnar artery are disposed near the surface on a palmar side, or a ventral side, of a wrist. Thus, the first biosignal may be measured from a ventral side of a wrist of a user.

The first sensor 110 measures the first biosignal using a light source and a light detector, a pressure sensor, a piezoelectric element, an impedance sensor or the like. In an example in which a light source and a light detector are used to measure the first biosignal, the first sensor 110 may measure a change in intensity of reflected light based on a change in blood perfusion to skin tissues using the light source configured to emit light to measure a photoplethysmogram (PPG) and the light detector configured to detect a light signal, for example, the reflected light, obtained when the light is reflected by the skin tissues of the user. The change in intensity of the reflected light may include pulse wave information. Here, the light source may emit, to the body, a light signal modulated based on a frequency, and the light detector may receive the light reflected by the body and convert the received reflected light to an electrical signal. For example, a photodiode or a phototransistor may be used as the light detector.

In an example in which a pressure sensor is used to measure the first biosignal, the first sensor 110 may detect a change in skin pressure due to a change in blood perfusion by using a pouch filled with a fluid transferring a pressure, a microelectromechanical systems (MEMS) pressure sensor, and the like. The change in pressure may include pulse wave information. In an example in which a piezoelectric element is used to measure the biosignal, the first sensor 110 may detect a surface displacement or a change in contact force based on a change in blood perfusion using the piezoelectric element, for example, a polyvinylidene fluoride (PVDF). The surface displacement or the change in contact force may include pulse wave information. The use of a pressure sensor or a piezoelectric element to measure the first biosignal may reduce the consumption of electric power in comparison to using a light source and a light detector.

In an example in which an impedance sensor is used to measure the first biosignal, the first sensor 110 may detect a change in impedance based on a change in blood flow in a blood vessel using the impedance sensor. The change in impedance may include pulse wave information. According to one example, the impedance sensor may include a pair of external electrodes configured to apply a high-frequency current to skin of the user and a pair of internal electrodes configured to measure a voltage drop occurring from the current along the skin.

The second sensor 120 measures a second biosignal including pulse wave information corresponding to at least one of vein, a capillary or both, herein referred to as venous or capillary pulse wave information. For example, the second sensor 120 may measure a second biosignal including a pulse wave component of a vein or a capillary from a dorsal side of the wrist of the user. Similar to the first sensor 110, the second sensor 120 measures the second biosignal using a light source and a light detector, a pressure sensor, a piezoelectric element, or an impedance sensor. The operation of the second sensor 120 depending on the type of sensor used is similar to that of the first sensor 110. Thus, repetitive descriptions will be omitted, and references may be made to the description of the first sensor 110 to determine the operation of the second sensor 120.

According to one example, one or both of the first sensor 110 and the second sensor 120 may include a plurality of sensor elements, and the sensor elements of both the first sensor 110 and the second sensor 120 may be sensors of a same type. For example, the first sensor 110 may include a plurality of sensor elements configured to measure a PPG signal at various measurement locations. In this example, the bioinformation estimator 130 may select a reference PPG signal to be used to estimate the bioinformation from among PPG signals to be transferred through a plurality of channels, and estimate the bioinformation based on the selected reference PPG signal. For example, the bioinformation estimator 130 may select, as the reference PPG signal, a PPG signal having a best signal quality, for example, a highest signal-to-noise ratio (SNR).

The bioinformation estimator 130 determines a time delay between the first biosignal measured through the first sensor 110 and the second biosignal measured through the second sensor 120, and estimates the bioinformation of the user based on the determined time delay. According to one example, the time delay may correspond to a pulse transit time taken by a pulse to propagate through a length of blood vessels. The bioinformation estimator 130 may include, for example, an operation algorithm for estimating the bioinformation of the user based on the time delay, a database, and a look-up table (LUT). The bioinformation estimator 130 may estimate, for example, an arterial stiffness, a vascular age, a blood pressure, a heart rate, a $SpO_2$, and a blood flow of the user, based on the determined time delay.

According to one example, the bioinformation estimator 130 may perform signal processing on the first biosignal and the second biosignal. Examples of the signal processing include filtering, amplification, and analog-to-digital conversion. Based on the signal processing, the bioinformation estimator 130 may determine the time delay based on biosignals obtained through the signal processing. The bioinformation estimator 130 may calculate the time delay between the first biosignal and the second biosignal by analyzing a waveform of the first biosignal and a waveform of the second biosignal. The time delay refers to a period of time that lapsed while a pulse wave measured in the first biosignal is reflected in the second biosignal.

According to one example, the bioinformation estimator 130 may extract a feature point from the waveform of the first biosignal and a corresponding feature point from the waveform of the second biosignal, and calculate a time delay based on the time that the feature points are extracted from the first biosignal and the second biosignal. In this example, feature points may include a peak point, a valley point, a maximum slope point, a minimum slope point or the like, which are extracted from waveforms of the biosignals. That is, the time delay may correspond to a pulse transit time taken by a pulse to appear as a feature point in the first biosignal and travel to appear as a corresponding feature point in the second biosignal. For example, the bioinformation estimator 130 may extract a maximum slope point from the waveform of the first biosignal and a minimum slope point from the waveform of the second biosignal, and calculate the time delay based on a time difference between the extracted maximum slope point and the extracted minimum slope point.

In another example, the bioinformation estimator 130 may move the waveform of the first biosignal or the waveform of the second biosignal along a time axis, and calculate the time delay based on a temporal movement value that allows a similarity between the waveforms to be maximal. The example will be described in more detail with reference to FIG. 9.

When the time delay between the first biosignal and the second biosignal is determined, the bioinformation estimator 130 estimates the bioinformation of the user from the time delay using a bioinformation estimation model. For example, the bioinformation estimator 130 may input time delay information to the bioinformation estimation model, and obtain the cardiovascular information such as the blood pressure, the arterial stiffness, and the vascular age from the bioinformation estimation model. The bioinformation estimator 130 estimates, based on the time delay, a trend in a change of pulse wave velocity over time, and estimates a change in the bioinformation of the user based on the estimated trend.

According to examples, the bioinformation measuring apparatus 100 may further include a user interface 140, a communication interface 150 or both. The user interface 140 receives information from the user or outputs the bioinformation.

The user interface 140 receives various inputs from the user. For example, the user interface 140 may receive user information necessary for estimating the bioinformation of the user. The user information may include information about, for example, an age, a height, a weight, and a gender of the user. The bioinformation estimator 130 determines the bioinformation of the user using the user information received from the user in addition to the measured first biosignal and the measured second biosignal.

The user interface 140 may include an input device and/or an output device, for example, a capacitive or a piezoelectric touch screen, a display panel, a touch pad, and a keyboard. The user interface 140 may configure a user interface screen to output the bioinformation under the control of the controller 160. Alternatively, the user interface 140 may output the bioinformation through a voice outputter, for example, a speaker.

The communication interface 150 transmits data to an external device and receives data from an external device. For example, the communication interface 150 may transmit data to a network or a wireless terminal such as a mobile device, a smart phone, a personal computer (PC), via wired or wireless communication such as Bluetooth or ZigBee. The communication interface 150 may further receive a command or data from the external device. The communication interface 150 may also transmit, to the external device, information about the measured biosignals such as, for example, waveform information and feature point information, and the time delay information and the estimated bioinformation.

The controller 160 controls an overall operation of the first sensor 110, the second sensor 120, the bioinformation estimator 130, the user interface 140, and the communication interface 150. For example, the controller 160 may control an activation or inactivation of the sensor elements included in the first sensor 110 and the second sensor 120, and electric power to be supplied to the sensor elements.

Figure 2:
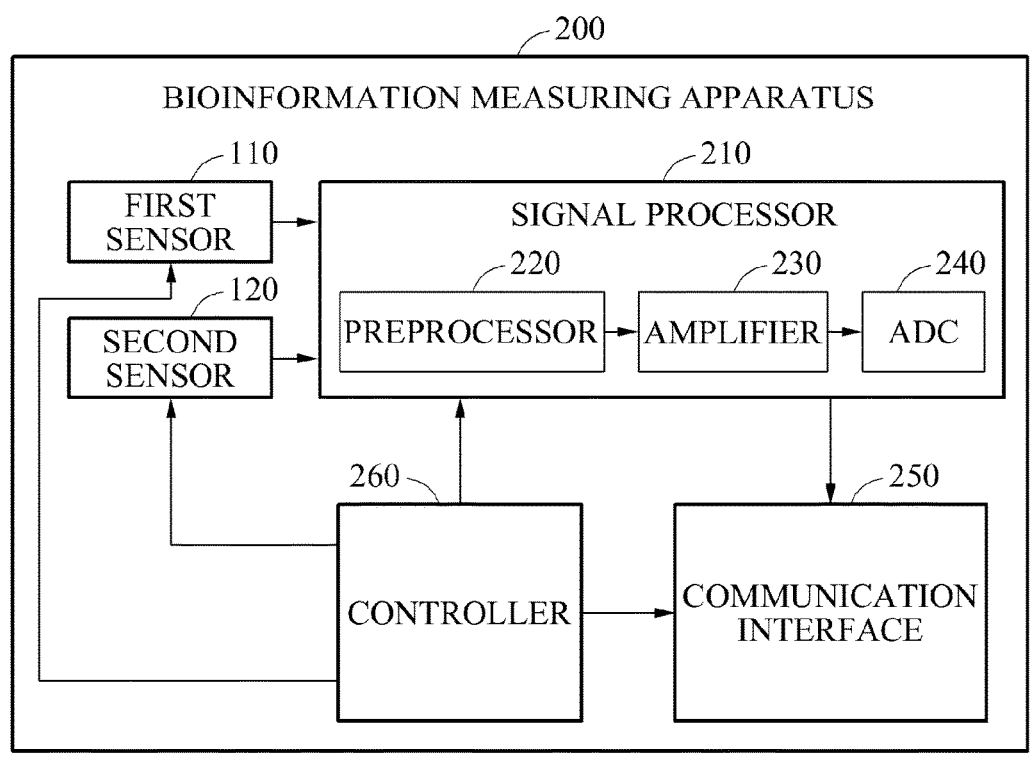
FIG. 2 is a diagram illustrating another example of an apparatus for measuring bioinformation.

FIG. 2 is a diagram illustrating another example of a bioinformation measuring apparatus 200. Referring to FIG. 2, the bioinformation measuring apparatus 200 includes a first sensor 110, a second sensor 120, a signal processor 210, a communication interface 250, and a controller 260.

The first sensor 110 measures a first biosignal including arterial pulse wave information, and the second sensor 120 measures a second biosignal including venous or capillary pulse wave information. For detailed operations of the first sensor 110 and the second sensor 120, reference may be made to the description of the first sensor 110 and the second sensor 120 provided with reference to FIG. 1.

The signal processor 210 performs signal processing on the first biosignal and the second biosignal. The signal processor 210 includes a preprocessor 220, an amplifier 230, and an analog-to-digital converter (ADC) 240.

According to one example, the preprocessor 220 converts electrical signals such as current signals, obtained from the first sensor 110 and the second sensor 120 into a voltage signal, and eliminate noise or obtain a necessary signal region by filtering the voltage signal. The amplifier 230 amplifies a signal transferred from the preprocessor 220, and the ADC 240 converts the signal amplified by the amplifier 230 to a digital signal.

The communication interface 250 transmits biosignal information that is converted to the digital signal to an external device through wired or wireless communication. The controller 260 controls an overall operation of the first sensor 110, the second sensor 120, the signal processor 210, and the communication interface 250.

Figure 3:
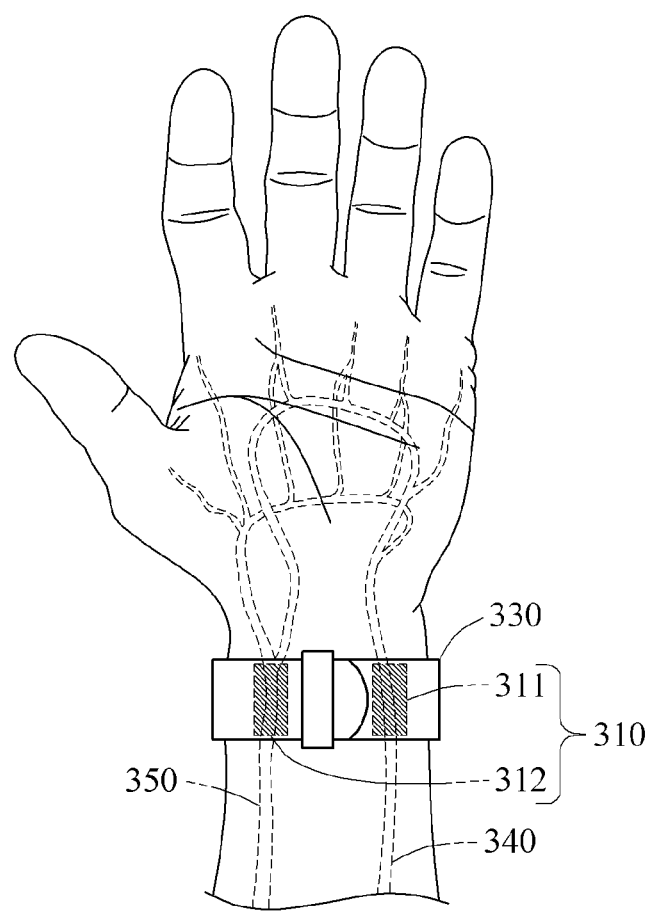
FIGS. 3 and 4 are diagrams illustrating an example of an apparatus for measuring bioinformation.
Figure 4:
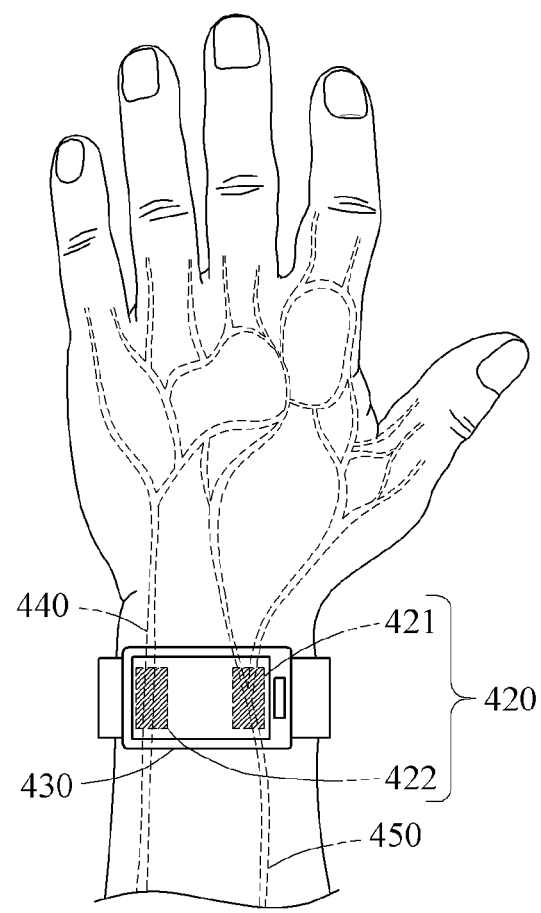
Figure 5:
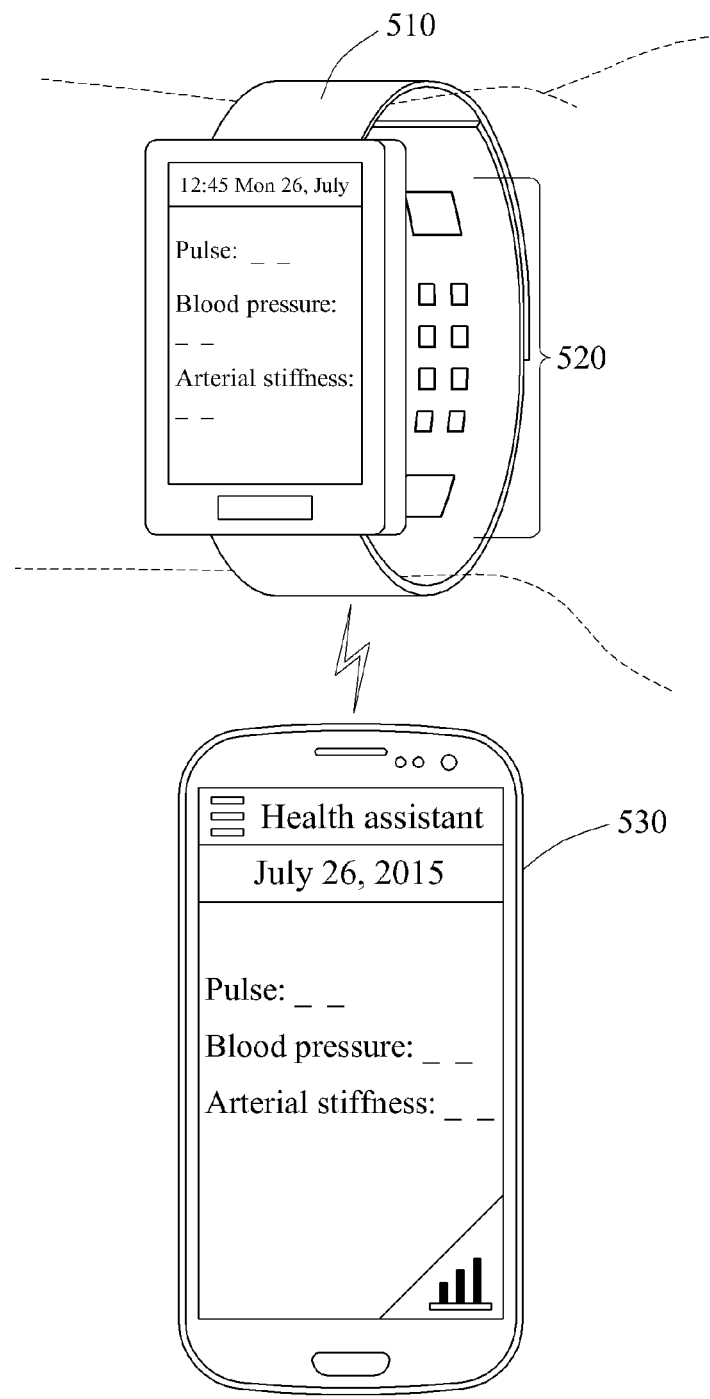
FIG. 5 is a diagram illustrating another example of an apparatus for measuring bioinformation.

FIGS. 3 through 5 are diagrams illustrating examples of a bioinformation measuring apparatus included in a wrist-type wearable device provided in a form of a watch.

According to one example, the bioinformation measuring apparatus measures a PPG or a body surface pressure wave including pulse wave information at two or more different measurement locations of a body surface of a user, and estimate bioinformation of the user based on a time delay between two or more signals measured at the different measurement locations. In this example, to secure sufficient time resolution, the measurement locations may need to be sufficiently separate from one another to have a sufficient time difference between the signals measured at the measurement locations. However, to increase a travel distance between the measurement locations as the pulse propagates through an arterial tree, a size of a measurement device may have to be increased or the signals measured at the measurement locations may not be sufficient for accurately deriving a time delay. Because wearable devices are generally miniaturized for convenience of users, such a configuration may not be suitable for continuous monitoring of the bioinformation of a user wearing a wearable device. The examples of bioinformation measuring apparatuses illustrated in FIGS. 3 through 5 may secure sufficient time delay between the signals measured at measurement locations, and also may narrow the external distance between the measurement locations, thereby keeping the size of the wearable device small in order to improve user convenience without deterioration in performance.

Referring to FIG. 3, a first sensor 310 is disposed on an inner side of a belt member such as a strap 330, of a wearable device, thereby allowing a user to wear the wearable device around a wrist of the user. When the user is wearing the wearable device, the first sensor 310 may measure a first biosignal including arterial pulse wave information corresponding to pulse wave in an artery from a palmar side of the wrist. The first sensor 310 may measure a pulse wave passing through an artery towards a distal end of a body of the user. The pulse wave may be from at least one of an ulnar artery 340 and a radial artery 350, which are disposed near the ventral surface of the wrist. In this example, two sensors or sensor elements 311 and 312 implements the first sensor 310.

In another example, the first sensor 310 may include a plurality of sensor elements that are arranged in an array. For example, three or more sensor elements may be arranged on a band or a strap of a wearable device. Using a plurality of sensor elements may, for example, improve an alignment of a sensor element with a blood vessel of interest and thereby to improve a quality of a signal to be obtained from the blood vessel. In addition, user convenience may also be improved because a user does not need to adjust a position of the wearable device around the wrist in order to accurately position the sensor elements 311 and 312 close to an ulnar artery 340 or a radial artery 350. A sensor element that is disposed closest to an ulnar artery or a radial artery may be used to obtain accurate measurements of a pulse wave.

According to one example, each sensor element includes a pair of a light source and a light detector to measure a PPG. For example, as the light source, an electrical light source such as a light-emitting diode (LED) and a laser diode or a chemical light source such as a fluorescent substance may be used. However, a type of the light source is not limited to the foregoing examples. In another example, the light source may emit infrared light or visible light in a red color to a body surface to measure a light signal from the ulnar artery 340 or the radial artery 350. A wavelength of the light emitted from the light source may be variously determined depending on a depth to penetrate into skin, a power efficiency, or the like.

According to another example, the first sensor 310 may measure a change in pulse wave signal based on a change in blood flow of the ulnar artery 340 or the radial artery 350 using a pressure sensor, a piezoelectric element, or an impedance sensor.

Referring to FIG. 4, a second sensor 420 configured to measure a second biosignal is disposed on a back side of a body 430 of the wearable device. In this example, the second sensor 420 includes sensor elements 421 and 422. When the user is wearing the wearable device, the second sensor 420 measures a second biosignal including pulse wave information from veins 440 and 450 or capillary in a dorsal side of the wrist of the user.

In another example, like the first sensor 310 illustrated in FIG. 3, the second sensor 420 may be implemented with a plurality of sensor elements that are arranged in an array. In yet another example, the second sensor 420 may be implemented with just one sensor element or three or more sensor elements. In another example, an array of a plurality of sensor elements is provided, and some of the sensor elements may function as a first sensor 310 and others may function as a second sensor 420, depending on whether a sensor element is suitably positioned to detect an arterial pulse wave or a venous or capillary pulse wave. Each sensor element may include a pair of a light source and a light detector to measure a PPG. According to one example, the light source of the second sensor 420 may emit visible light in a green color having a shorter wavelength than the light emitted from the light source of the first sensor 310. However, the wavelength of the light to be emitted from the light source of the second sensor 420 is not limited to the foregoing example.

In another example, the second sensor 420 may measure a change in pulse wave signal based on a change in blood flow of the veins 440 and 450 or the capillary blood using a pressure sensor, a piezoelectric element, or an impedance sensor.

Anatomically, arteries such as the ulnar artery 340 and the radial artery 350 illustrated in FIG. 3 pass near a ventral surface of the wrist, form an arch inside a flesh portion of a palm, and extend towards respective sides of each finger in smaller arteries and capillaries. Blood supplied to a hand through the artery returns to the heart after passing through the wrist region again, in veins, after having passed through capillaries. Referring to FIG. 4, a large artery is not positioned in the dorsal side of the wrist, and a wrist ligament surrounds a dorsal portion of the wrist; thus, the second biosignal measured by the second sensor 420 from the dorsal side of the wrist may reflect a pulse wave component passing through the veins 440 and 450 or the capillaries more than a pulse wave component passing through major arteries.

Thus, a time delay between the first biosignal obtained through the first sensor 310 illustrated in FIG. 3 and the second biosignal obtained through the second sensor 420 illustrated in FIG. 4 may have a high correlation with an actual time delay between a pulse wave in an artery propagating towards the hand and a pulse wave in a vein or a capillary propagating towards the heart after passing through a distal end of the hand. The bioinformation measuring apparatus may thus readily estimate bioinformation of the user using the first biosignal including arterial pulse wave information measured from one or more arteries near the ventral surface of the wrist and the second biosignal including venous or capillary pulse wave information measured from veins 440 and 450 or capillaries near the dorsal side of the wrist, thereby enabling a miniaturization of the wearable device while obtaining an accurate measurement.

Referring to FIG. 5, a wearable device 510 determines a time delay between a first biosignal as a pulse passes an artery near a ventral surface of a wrist of a user as described with reference to FIG. 3 and a second biosignal as the pulse passes through a vein or a capillary near a dorsal surface of the wrist as described with reference to FIG. 4, and estimates cardiovascular information such as a pulse, a blood pressure, and an arterial stiffness based on the determined time delay.

In this example, the wearable device 510 includes a plurality of sensors 520 to measure a biosignal or other signals, in addition to the first biosignal and the second biosignal detected by the first sensor and the second sensor as described with reference to FIGS. 3 and 4. The sensor 520 may include, for example, an inertial sensor or movement sensor configured to measure movement information of the user or a temperature sensor configured to move a temperature of the user. The wearable device 510 estimates the bioinformation of the user by analyzing a waveform of a pulse wave signal to be measured through the sensor 520, and output the estimated bioinformation through a display.

The wearable device 510 may provide the user with the estimated bioinformation through a mobile device 530. The mobile device 530 may verify a health state of the user by analyzing the bioinformation received from the wearable device 510, and record a change in the bioinformation with respect to time.

In the example illustrated in FIG. 5, the wearable device 510 provides the user with the bioinformation estimated by the wearable device 510 through interworking with the mobile device 530. However, the configuration of the wearable device is not limited thereto; in another example, the bioinformation estimated by the wearable device 510 may be provided to the user through an application installed in a device that interworks with the wearable device 110 such as, for example, a PC, a tablet PC, and a smart television (TV).

Further, the examples of apparatuses for measuring bioinformation described above may be provided in other types of wearable devices, such as a band, a bracelet, a cuff, an anklet and devices that encircle a body part of a user, such as an arm, a leg, a wrist, a knee, an ankle, or a neck. The wearable devices are not limited to wrist-type wearable devices illustrated in FIGS. 3 through 5. For example, an anklet or a bracelet may be used to measure the first and second biosignals from an artery and a vein or a capillary near a surface of an ankle or a wrist. According to one example, the first and second biosignals may be measured from substantially the same section of a body part. In this example, considering a wrist to be a section of a lower arm, both the first and second biosignals may be measured from the wrist, rather than one of the biosignal being measured from a finger or an upper arm. Because the first biosignal includes arterial pulse wave information and the second biosignal includes venous or capillary pulse wave information, a time delay may be accurately estimated even though the physical locations for taking the first and second biosignals are close to each other.

Figure 6:
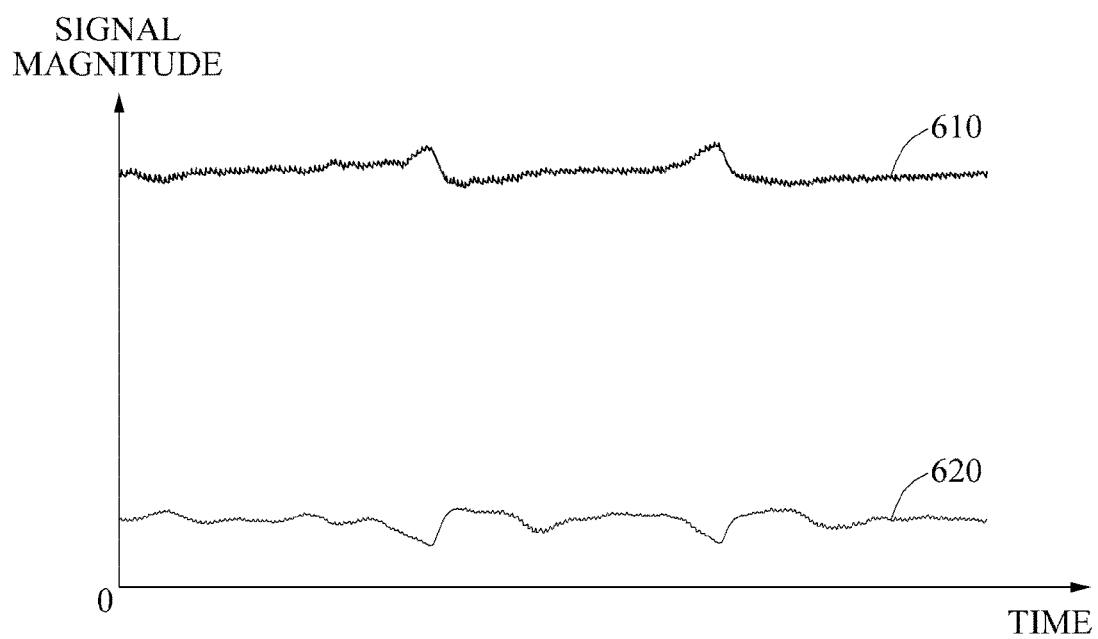
FIGS. 6 through 8 are diagrams illustrating examples of processes of determining a time delay between biosignals by a bioinformation estimator.
Figure 7:
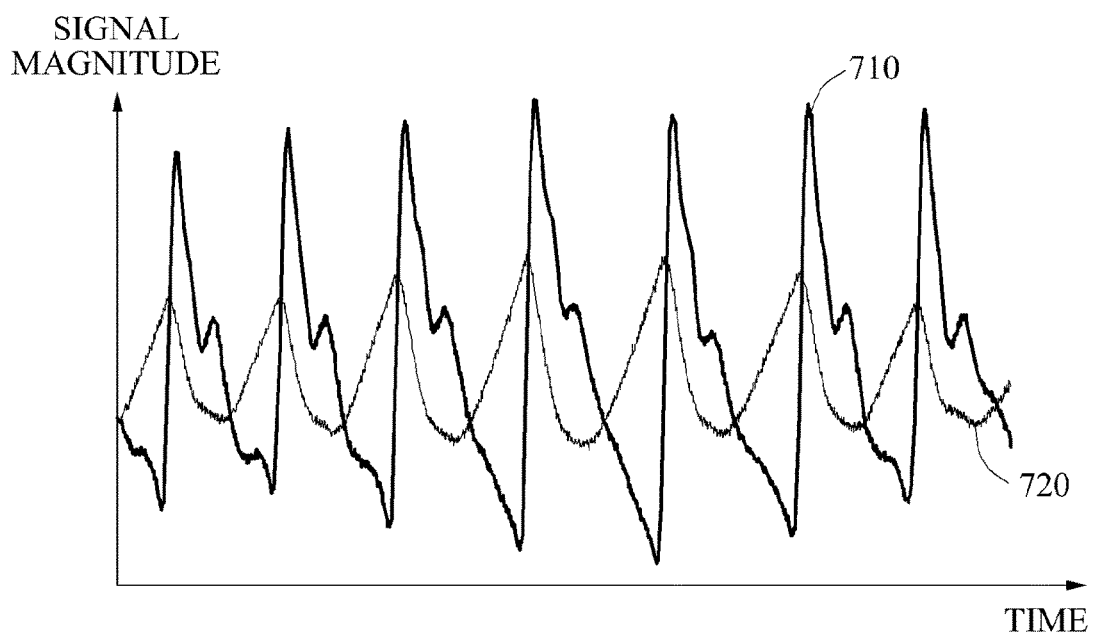
Figure 8:
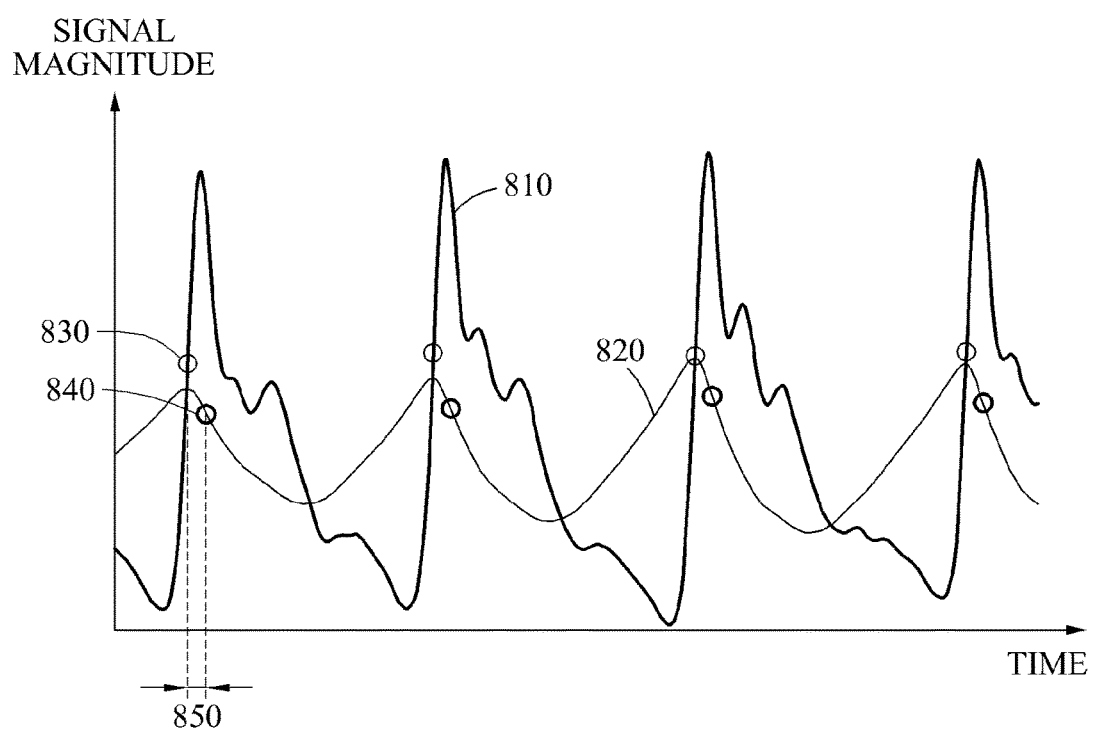

FIGS. 6 through 8 are diagrams illustrating examples of processes of determining a time delay between biosignals performed by a bioinformation estimator.

FIG. 6 illustrates an example of a PPG waveform measured as a first biosignal 610 by a first sensor in a palmar side of a wrist of a user and an example of a PPG waveform measured as a second biosignal 620 by a second sensor in a dorsal side of the wrist. A bioinformation measuring apparatus may continuously measure the first biosignal 610 and the second biosignal 620 while a user is wearing the bioinformation measuring apparatus on his or her wrist. In this example, the first biosignal 610 includes pulse wave information based on a change in blood flow in an artery, and the second biosignal 620 includes pulse wave information based on a change in blood flow in a vein or a capillary. Since a blood flow in a blood vessel changes over time based on the repetitive contractions and relaxations of the heart, pulse waveforms illustrated in FIG. 6 may be detected in an artery or a vein.

FIG. 7 illustrates an example of a waveform corresponding to a first signal 710 that is obtained by performing detrending and low-pass filtering on the first biosignal 610 illustrated in FIG. 6 and an example of a waveform corresponding to a second signal 720 that is obtained by performing detrending and low-pass filtering on the second biosignal 620 illustrated in FIG. 6. The detrending and low-pass filtering may be performed by a bioinformation estimator. The detrending is a signal processing method to eliminate a base component from a frequency domain of a signal. In this example, it is assumed that a method of eliminating a trend signal including a low-frequency component from an original signal is used to perform the detrending. However, the scope of examples is not limited thereto, and signal waveforms such as in the first signal 710 and the second signal 720 illustrated in FIG. 7 may be obtained through band-pass filtering.

Referring to FIG. 8, a bioinformation estimator may use a feature point extracted from each of a first biosignal 810 and a second biosignal 820 to calculate a time delay between the first biosignal 810 and the second biosignal 820. The bioinformation estimator may extract feature points from respective waveforms of the first biosignal 810 and the second biosignal 820 corresponding to the first signal 710 and the second signal 720 illustrated in FIG. 7, and may determine a time delay between the first biosignal 810 and the second biosignal 820 based on the extracted feature points. In this example, the time delay corresponds to a pulse transit time taken by a feature point of a pulse detected in the first biosignal 810 to propagate and be detected in the second biosignal 820.

For example, referring to FIG. 8, the bioinformation estimator may extract, as a feature point, a positive maximum slope point 830 from the waveform of the first biosignal 810 and a negative minimum slope point 840 from the waveform of the second biosignal 820. The bioinformation estimator may determine a time delay between the appearance of the positive maximum slope point 830 in the first biosignal 810 and the appearance of the negative minimum slope point 840 in the second biosignal 820 based on a time difference 850 between the positive maximum slope point 830 extracted from the first biosignal 810 and the negative minimum slope point 840 extracted from the second biosignal 820. The bioinformation estimator may continuously determine time delay information between the first biosignal 810 and the second biosignal 820 over time by repetitively performing the foregoing process on other feature points of the first biosignal 810 and the second biosignal 820.

In another example, the bioinformation estimator extracts, as a feature point, a peak point, a valley point, a maximum slope point, or a minimum slope point from the waveforms of the first biosignal 810 and the second biosignal 820, and determines the time delay between the first biosignal 810 and the second biosignal 820 based on the extracted feature point. A method of extracting a feature point from a waveform of a first biosignal and a waveform of a second biosignal is not limited to the foregoing examples; thus, the bioinformation estimator may determine a time delay using various types of feature points.

Figure 9:
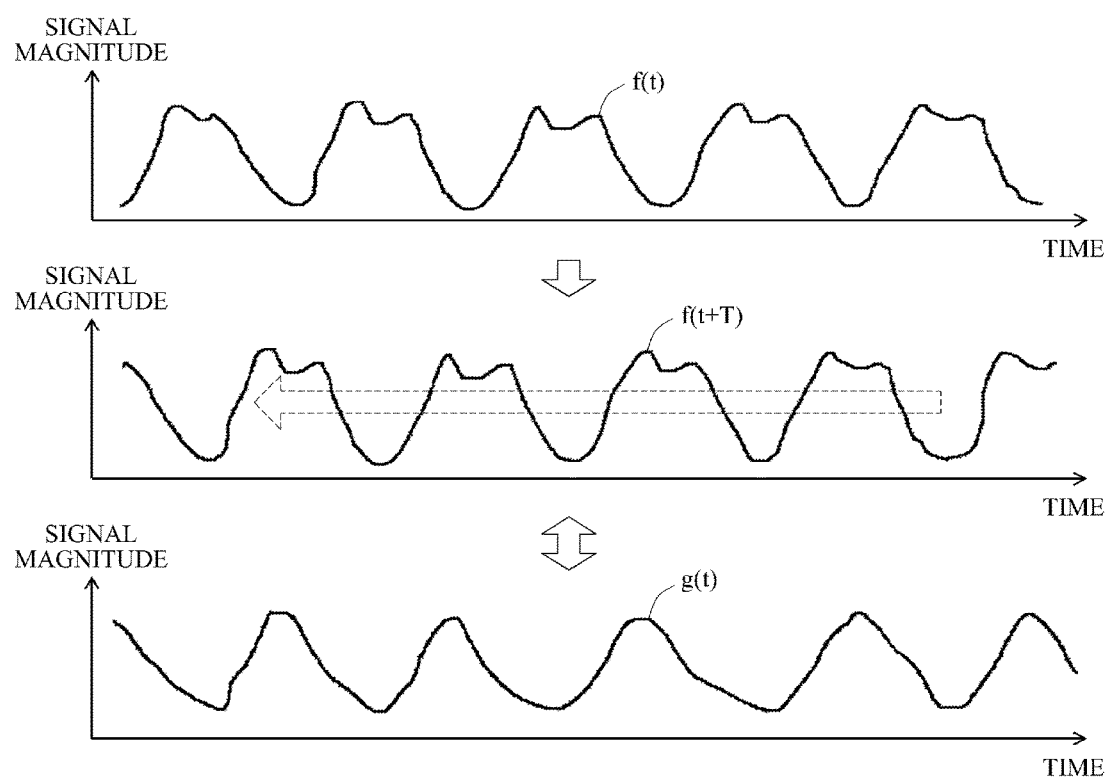
FIG. 9 is a diagram illustrating another example of a process of determining a time delay between biosignals by a bioinformation estimator.

FIG. 9 is a diagram illustrating another example of a process of determining a time delay between biosignals by a bioinformation estimator.

The bioinformation estimator may use a similarity between signal waveforms to determine a time delay between a first biosignal and a second biosignal, without using a feature point as described with reference to FIG. 8. Using the similarity between the signal waveforms in lieu of the feature point, the time delay between the first biosignal and the second biosignal may be robustly determined against noise.

Referring to FIG. 9, an example of a waveform f(t) corresponding to a first biosignal and an example of a waveform g(t) corresponding to a second biosignal are illustrated. In addition, an example of a waveform f(t+T) obtained by moving a waveform f(t) by T along a time axis is illustrated. In this example of process of determining a time delay between biosignals, the bioinformation estimator calculates an integral value of a value resulting from a dot product calculation between f(t+T) and g(t), and determines a time delay between the first biosignal and the second biosignal based on the calculated integral value.

Based on a change in integral value based on a change in T, an integral value may be large in a case of waveforms f(t+T) and g(t) being in phase, and an integral value may be small in a case of waveforms f(t+T) and g(t) being out of phase. When a correlation between waveforms f(t+T) and g(t) increases, the integral value also increases. The bioinformation estimator may determine a value of the time delay to correspond to a value of T that has a first integral value at a maximum point among integral values based on T. A method of calculating a similarity between waveforms f(t+T) and g(t) is not limited to a method using an integral value as described in the foregoing example; various other methods may be used in another example.

Figure 10:
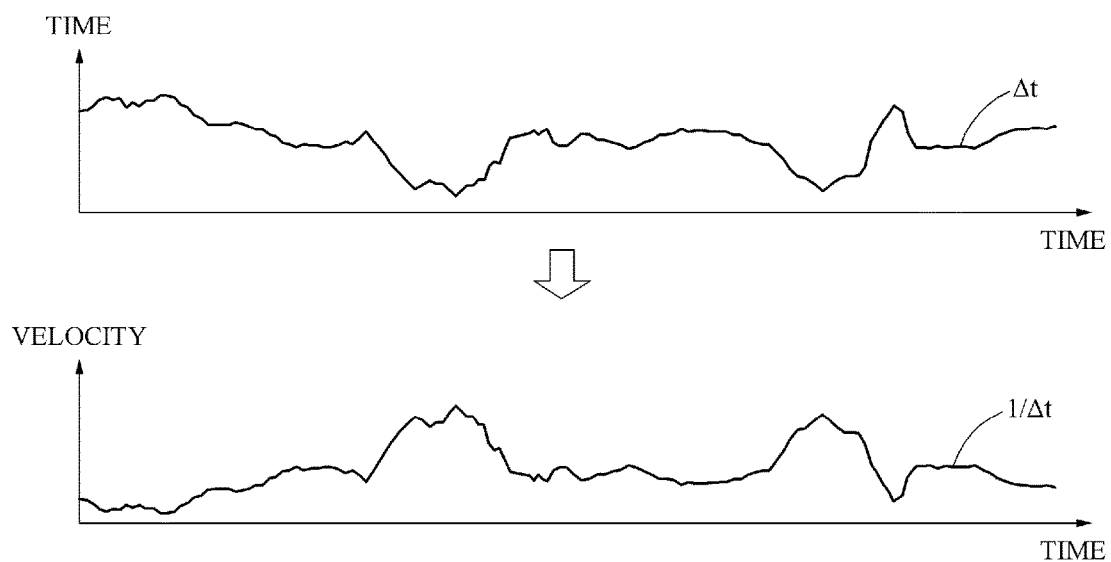
FIG. 10 is a diagram illustrating an example of a process of deriving, by a bioinformation estimator, velocity information from time delay information between biosignals.

FIG. 10 is a diagram illustrating an example of a process of deriving velocity information from time delay information. The process of deriving the velocity information may be performed by a bioinformation estimator.

Referring to FIG. 10, the time delay between a first biosignal and a second biosignal is continuously estimated over time, and illustrated as Δt in the upper graph. The lower graph of FIG. 10 illustrates a result of inverting the time delay value Δt. Assuming a distance traveled by a pulse wave to be substantially constant over time, the inverse of time delay value, 1/Δt, correlates with a velocity of the pulse wave. Thus, in this example, velocity information may be derived from an inverse value of the time delay value. The bioinformation estimator may estimate bioinformation of a user based on the derived velocity information. For example, a degree of change that takes place in the bioinformation of a user over a given time period may be determined by estimating a degree of change that takes place in the velocity information over the given time period. Thus, in response to obtaining a reference value of an average blood pressure of the user, the bioinformation estimator may determine a trend in a change of the average blood pressure of the user by applying a trend in a change in the derived velocity information to the reference value of the average blood pressure.

Figure 11:
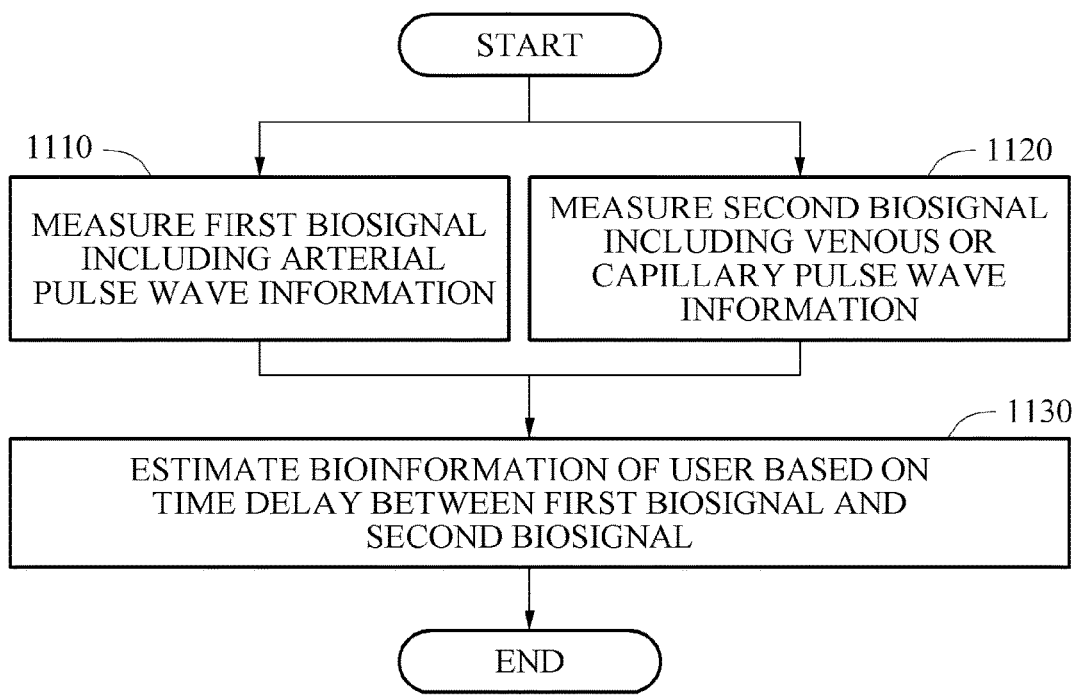
FIG. 11 is a flowchart illustrating an example of a method of measuring bioinformation.

FIG. 11 is a flowchart illustrating an example of a method of measuring bioinformation. The method may be performed by a bioinformation measuring apparatus including at least one processor.

Referring to FIG. 11, in operation 1110, the bioinformation measuring apparatus measures a first biosignal including arterial pulse wave information. For example, the bioinformation measuring apparatus may measure the arterial pulse wave information from at least one of a radial artery and an ulnar artery disposed near a ventral surface of a wrist of a user, using a light source and light detector, a pressure sensor, a piezoelectric element, or an impedance sensor to detector a PPG.

In operation 1120, the bioinformation measuring apparatus measures a second biosignal including venous or capillary pulse wave information. For example, the bioinformation measuring apparatus may measure the venous or capillary pulse wave information from at least one of a vein and a capillary located near a dorsal surface of the wrist, using a light source and light detector, a pressure sensor, a piezoelectric element, or an impedance sensor to detect a PPG.

In operation 1130, the bioinformation measuring apparatus determines a time delay between the first biosignal and the second biosignal, and estimates bioinformation of the user based on the determined time delay. For example, the bioinformation measuring apparatus may extract feature points from a waveform of the first biosignal and a waveform of the second biosignal, and determine the time delay based on a distance between the feature points. Alternatively, the bioinformation measuring apparatus may move the waveform of the first biosignal or the waveform of the second biosignal along a time axis, and determine the time delay based on a time movement value that allows a similarity between the waveforms to be maximal. When the time delay between the first biosignal and the second biosignal is determined, the bioinformation measuring apparatus may estimate the bioinformation such as, for example, a blood pressure, an arterial stiffness, and a vascular age of the user, from the time delay using a bioinformation estimation model. For example, the bioinformation estimation model may set an average blood pressure value of the user to be a reference value, and determine a trend in a change of average blood pressure value by applying, to the set reference value, a trend in a change of velocity derived from the time delay between the first biosignal and the second biosignal. Also, by applying a preset weight to a variation between a velocity at a first point in time and a velocity at a second point in time, a variation of the average blood pressure in a section between the first point and the second point may be determined.

For details not described in operations 1110 through 1130, reference may be made to the details described with reference to FIGS. 1 through 10.

As a non-exhaustive example only, a wearable device as described herein may be a mobile smart device such as a ring, a watch, a bracelet, an ankle bracelet, a belt, a necklace, a helmet, or a device embedded in clothing. In one example, a wearable device is a device that is designed to be mountable directly on the body of the user, such as a bracelet or a watch. A wearable device may or may not include a display. A display may be implemented using a liquid crystal display (LCD), a light-emitting diode (LED) display, a touch screen, or any other type of display configured to display the images and information. A screen may be a physical structure that includes one or more hardware components that provide the ability to render a user interface and receive user input.

The bioinformation estimator, controller, user interface, communication interface, signal processor, preprocessor, amplifier, analog-to-digital converter, first sensor, second sensor, bioinformation measuring apparatus, input device, output device, display and other components, units and apparatuses illustrated in FIGS. 1-5 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, circuits, sensors, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 6-11 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

What is claimed is:

1. An apparatus for measuring bioinformation, the apparatus comprising:
   a first sensor configured to measure a first biosignal comprising arterial pulse wave information from a ventral side of a wrist;
   a second sensor configured to measure a second biosignal comprising venous or capillary pulse wave information from a dorsal side of the wrist; and
   a bioinformation estimator, implemented at a processor, configured to estimate bioinformation of a user based on a time delay between the first biosignal and the second biosignal.

2. The apparatus of claim 1, wherein the arterial pulse wave information comprises pulse wave information from a radial artery or an ulnar artery.

3. The apparatus of claim 1, wherein the venous or capillary pulse wave information comprises pulse wave information from a vein or a capillary.

4. The apparatus of claim 1, wherein the first sensor is disposed in a strap of a wrist-type wearable device, and the second sensor is disposed on a back side of a body of the wrist-type wearable device.

5. The apparatus of claim 1, wherein the first sensor comprises:
   a first light source configured to emit first light to measure a photoplethysmogram; and
   a first light detector configured to detect first reflected light corresponding to the first light reflected by a body part of the user.

6. The apparatus of claim 5, wherein the second sensor comprises:
   a second light source configured to emit second light to measure a photoplethysmogram; and
   a second light detector configured to detect second reflected light corresponding to the second light reflected by a body part of the user,
   wherein the second light has a shorter wavelength than the first light.

7. The apparatus of claim 1, wherein the first sensor is further configured to measure the first biosignal using at least one of a pressure sensor, an impedance sensor, or a piezoelectric element.

8. The apparatus of claim 1, wherein the second sensor is further configured to measure the second biosignal using at least one of a pressure sensor, an impedance sensor, or a piezoelectric element.

9. The apparatus of claim 1, wherein the bioinformation estimator is further configured to estimate a trend in a change of pulse wave velocity over time based on the time delay between the first biosignal and the second biosignal, and to estimate a change in the bioinformation of the user based on the estimated trend.

10. The apparatus of claim 1, wherein the bioinformation estimator is further configured to determine the time delay based on a feature point extracted from a waveform of the first biosignal and a feature point extracted from a waveform of the second biosignal.

11. The apparatus of claim 10, wherein the bioinformation estimator is further configured to estimate the bioinformation based on a time delay between a maximum slope point of the waveform of the first biosignal and a minimum slope point of the waveform of the second biosignal.

12. The apparatus of claim 1, wherein the bioinformation estimator is further configured to move at least one of a waveform of the first biosignal and a waveform of the second biosignal along a time axis, and to determine the time delay based on a similarity between the at least one moved waveform of the first biosignal and the waveform of the second biosignal.

13. The apparatus of claim 1, wherein the bioinformation estimator is further configured to estimate at least one of an arterial stiffness, a vascular age, a blood oxygen saturation level ($SpO_2$), a heart rate, and a blood pressure of the user based on the time delay.

14. The method of claim 1, wherein the first sensor is further configured to be disposed on a ventral side of a wrist, and the second sensor further configured to be disposed on a dorsal side of the wrist.

15. An apparatus for measuring bioinformation, the apparatus comprising:
   a first sensor configured to measure a first biosignal comprising arterial pulse wave information from a ventral side of a wrist;
   a second sensor configured to measure a second biosignal comprising venous or capillary pulse wave information from a dorsal side of the wrist; and
   a signal processor configured to convert the first biosignal and the second biosignal into respective digital signals, and to estimate bioinformation of a user based on a time delay between the respective digital signals.

16. The apparatus of claim 15, wherein the signal processor is further configured to amplify the first biosignal and the second biosignal before converting the first biosignal and the second biosignal into the respective digital signals.

17. The apparatus of claim 15, wherein the first sensor is disposed inside a strap of a wrist-type wearable device, and the second sensor is disposed on a back side of a body of the wrist-type wearable device.

18. A method of measuring bioinformation, the method comprising:
   measuring a first biosignal from a ventral side of a wrist, the first biosignal comprising arterial pulse wave information;
   measuring a second biosignal from a dorsal side of the wrist, the second biosignal comprising venous or capillary pulse wave information; and
   estimating bioinformation of a user based on a time delay between the first biosignal and the second biosignal.

19. The method of claim 18, wherein the arterial pulse wave information comprises pulse wave information from a radial artery or an ulnar artery.

20. The method of claim 1, wherein the venous or capillary pulse wave information comprises pulse wave information from a vein or a capillary.

21. A non-transitory computer-readable medium storing instructions that, when executed by a processor, causes a processor to perform the method of claim 18.

22. A wearable device comprising:
   one or more sensors configured to detect a first pulse wave information from an artery at a ventral side of a wrist and a second pulse wave information from a vein or capillary at a dorsal side of the wrist; and
   a processor configured to estimate a pulse transit time for a pulse detected in the first pulse wave information to propagate and be reflected in the second pulse wave information and to estimate bioinformation of a user based on the pulse transit time.

23. The device of claim 22, wherein the processor is further configured to estimate cardiovascular information based on an inverse value of the pulse transit time.

24. The device of claim 22, wherein the wearable device is configured to position each of the one or more sensors on one body location of a user.

25. A method of measuring bioinformation, the method comprising:
- obtaining first pulse wave information from an artery at a ventral side of a wrist and second pulse wave information from a vein or a capillary at a dorsal side of the wrist;
- using a processor to estimate a pulse transit time based on the first pulse wave information and the second pulse wave information; and
- estimating bioinformation based on the estimated pulse transit time.

26. The method of claim 25, wherein the obtaining of the first and second pulse wave information comprises using sensors of a wearable device to measure a biosignal.

27. The method of claim 25, wherein both the first pulse wave information and the second pulse information are obtained from one body location of the user.

28. The method of claim 25, wherein the obtaining of the first and second pulse wave information is performed by a wearable device, and
- the estimating of the bioinformation is performed by a terminal that wirelessly receives data from the wearable device.

* * * * *